United States Patent [19]
Tianbao et al.

[11] Patent Number: 5,612,378
[45] Date of Patent: Mar. 18, 1997

[54] BIS-ARYLSULFONYLAMINOBENZAMIDE DERIVATIVES AND THE USE THEREOF AS FACTOR Xa INHIBITORS

[75] Inventors: Lu Tianbao, Exton, Pa.; Richard M. Soll, Lawrenceville, N.J.

[73] Assignee: 3-Dimensional Pharmaceuticals, Inc., Exton, Pa.

[21] Appl. No.: 470,579

[22] Filed: Jun. 6, 1995

[51] Int. Cl.$^6$ .......................... A61K 31/18; C07C 311/16
[52] U.S. Cl. .......................... 514/602; 514/255; 514/604; 514/821; 514/822; 514/836; 514/886; 544/358; 544/398; 544/399; 544/400; 564/80; 564/82
[58] Field of Search .......................... 564/82, 80; 544/358, 544/400, 398, 399, 255; 514/255, 602, 604, 821, 822, 834, 886

[56] References Cited

U.S. PATENT DOCUMENTS

| | | | |
|---|---|---|---|
| 4,544,654 | 10/1985 | Davey et al. | 514/210 |
| 4,977,168 | 12/1990 | Bernat et al. | 514/330 |
| 5,371,091 | 12/1994 | Misra et al. | 514/314 |
| 5,385,885 | 1/1995 | Gasic et al. | 514/12 |

FOREIGN PATENT DOCUMENTS

| | | |
|---|---|---|
| WO93/15756 | 8/1993 | WIPO . |
| WO94/13693 | 6/1994 | WIPO . |
| WO94/17817 | 8/1994 | WIPO . |
| WO94/20526 | 9/1994 | WIPO . |
| WO94/20535 | 9/1994 | WIPO . |

OTHER PUBLICATIONS

Church and Hoffman, Heparin Cofactor II and Thrombin: Heparin Binding Proteins Linking Hemostasis and Inflammation, *Trends in Cardiovascular Medicine* 4(3):140–146 (1993).
Claeson G. Synthetic peptides and peptidomimetics as substrates and inhibitors of thrombin and other proteases in the blood coagulation system, *Blood Coagulation and Fibrinolysis* 5(411–436 (Jun. 1994).
Coughlin in S.R., Molecular Mechanisms of Thrombin Signaling, *Seminars in Hematology* 31(4):270–277 (Oct. 1994).
Hara et al., DX–9065a, a New Synthetic, Potent Anticoagulant and Selective Inhibitor for Factor Xa, *Thrombosis and Hemostasis* 71:314–319 (Mar. 1994).
Harker L. A., Strategies for inhibiting the effects of thrombin, *Blood Coagulation and Fibrinolysis* 5 (Suppl 1):s47–s58 (Jan. 1994).
Lefkovits and Topol, Direct Thrombin Inhibitors in Cardiovascular Medicine, *Circulation* 90(3):1522–1536 (Sep. 1994).
Markwardt F., Inventory of Coagulation Inhibitors from Animals Feeding on Blood, *Thrombosis and Hemostasis* 72(3):477–479 (Sep. 1994).
Mellott et al., Acceleration of Recombinant Tissue–Type Plasminogen Activator–Induced Reperfusion and prevention of Reocclusion by Recombinant Antistasin, a Selective Factor Xa Inhibitor, in a Canine Model of Femoral Arterial Thrombosis, *Circulation Research* 70:1152–1160 (1992).
Nagahara et al., (Amidinoaryl)propanoic Acid Derivatives as Novel Blood Coagulation Factor Xa Inhibitors, *Journal of Medicinal Chemistry* 37:1200–1207 (Apr. 1994).
Ragosta et al., Specific Factor Xa Inhibition Reduces Restenosis After Ballon Angioplasty of Atherosclerotic Femoral Arteries in Rabbits, *Circulation* 89:1262–1271 (Mar. 1994).
Raj et al., Long–term Oral Anticoagulant Therapy: Update on Indicators, Therapeutic Ranges, and Monitoring, *The American Journal of the Medical Sciences* 307(2):128–32 (Feb. 1994).
Seymour et al., Ecotin Is a Potent Anticoagulant and Reversible Tight–Binding Inhibitor of Factor Xa, *Biochemistry* 33:3949–3958 (Apr. 1994).
Sitko et al., Conjunctive Enhancement of Enzymatic Thrombolysis and Prevention of Thrombotic Reocclusion With the Selective Factor Xa Inhibitor, Tick Anticoagulant Peptide, *Circulation* 85:805–815 (1992).
Stürzebecher et al., Synthetic Inhibitors of Bovine Factor Xa and Thrombin Comparison of Their Anticoagulant Efficiency, *Thrombosis Research* 54:245–252 (1989).
Tapparelli et al., Synthetic Low–molecular weight thrombin inhibitors: molecular design and pharmacological profile, *Trends in Pharmacological Sciences* 14:366–376 (1993).
Tidwell et al., Strategies for Anticoagulation with Synthetic Protease Inhibitors, Xa Inhibitors versus Thrombin Inhibitors, *Thrombosis Research* 19:339–349 (1980).
Weitz and Hirsh, New Anticoagulant Strategies, *Journal of Laboratory Clilnical Medicine* 122(4):364–373 (1993).
Yamazaki et al., Effects of DX–9065a, on Orally Active, Newly Synthesized and Specific Inhibitor of Factor Xa, against Experimental Disseminated Intravascular Coagulation in Rats, *Thrombosis and Hemostasis* 72(3):393–396 (Sep. 1994).

*Primary Examiner*—José G. Dees
*Assistant Examiner*—Lily Ledynh
*Attorney, Agent, or Firm*—Sterne, Kessler, Goldstein & Fox P.L.L.C.

[57] ABSTRACT

The present invention is directed to non-peptidic factor Xa inhibitors which are useful for the treatment of arterial and venous thrombotic occlusive disorders, inflammation, cancer, and neurodegenerative diseases. The factor Xa inhibitors provide compounds of structure:

wherein each $R^1$ is independently one of alkyl, substituted alkyl, cycloalkyl, aryl, substituted aryl, heteroaryl or substituted heteroaryl;

each $R^2$ and $R^3$ is independently one of hydrogen, alkyl, aryl or arylalkyl;

Y is a bond, or is one of $-(CH_2)_p-$, cycloalkyl, aryl or $C_{2-10}$ heterocycle; and m, n and p are each independently 1 to 10.

10 Claims, No Drawings

BIS-ARYLSULFONYLAMINOBENZAMIDE DERIVATIVES AND THE USE THEREOF AS FACTOR XA INHIBITORS

FIELD OF THE INVENTION

The present invention relates to compounds that are inhibitors of thrombin production via factor Xa inhibition, their pharmaceutically acceptable salts, and pharmaceutically acceptable compositions thereof. The compounds and compositions are useful in the treatment of arterial and venous thrombotic occlusive disorders, inflammation and cancer.

BACKGROUND OF THE INVENTION

The serine protease thrombin occupies a central role in hemostasis and thrombosis (Tapparelli et al., Trends in Pharmacological Sciences 14:366–376 (1993); Lefkovits and Topol, Circulation 90(3):1522–1536 (1994); Harker, Blood Coagulation and Fibrinolysis 5 (Suppl 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, Seminars in Hematology 31(4):270–277 (1994)), and autoamplifies its own production through a feedback mechanism.

As a multifactorial protein, thrombin induces a number of effects on platelets, endothelial cells, smooth muscle cells, leukocytes, the heart, and neurons (Tapparelli et at., Trends in Pharmacological Sciences 14:366–376 (1993); Church and Hoffman, Trends in Cardiovascular Medicine 4(3):140–146 (1993)). Platelet activation leads to shape change and aggregation as well as the synthesis, release and secretion of vasoactive substances and lysosomal enzymes. Endothelial cell activation results in the secretion of stimulatory agents leading to increased vascular permeability and adhesiveness for mononuclear cells, one consequence of which is extravasation of leukocytes at the site of thrombin generation. Thrombin induces fibroblast and smooth muscle cell proliferation suggesting that thrombin plays a key role in lesion development following vascular damage. Enhanced automaticity and prolongation of repolarization have been observed in cardiac myocytes showing sensitivity to thrombin. Normal neuronal development has been shown also to be influenced by thrombin. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoaguability during chemotherapy; Alzheimer's disease; and Down's syndrome.

To date only three classes of compounds (heparins, low-molecular weight heparins, and coumarins, such as warfarin) have been used in anticoagulant therapy. Each class has severe limitations and liabilities (Weitz and Hirsh, Journal of Laboratory Clinical Medicine 122:364–373 (1993); Raj et al., The American Journal of the Medical Sciences 307(2):128 (1994)). All three classes indirectly inhibit thrombin. Heparin and low-molecular weight heparins augment antithrombin III and/or heparin cofactor II inhibition of thrombin, whereas coumarins inhibit vitamin K-dependent post-translational modification. Close monitoring and titration of therapeutic doses is required when employing these agents due to patient variability. Hemorrhagic complications due to bleeding are an encountered side effect. In fact, bleeding remains as the most common side effect of long term oral anticoagulant therapy. Lack of activity in arterial thrombosis in the case of heparin is due to its inability to inhibit clot bound thrombin. Lack of oral activity in the case of heparins and low-molecular weight heparins preclude their use for chronic administration.

Direct thrombin inhibitors of various structural classes have been identified recently (Tapparelli et al., Trends in Pharmacological Sciences 14:366–376 (1993); Claeson, Blood Coagulation and Fibrinolysis 5:411–436 (1994); Lefkovits and Topol, Circulation 90(3):1522–1536 (1994)). Representative compounds that act by inhibiting the active site of thrombin include the α-chloroketone D-phenylalanyl-L-prolyl-L-arginyl chloromethylketone (PPACK), the boro-arginine DUP714, the peptide arginal GYK114766, the cyclic peptides cyclotheonamides A and B, the benzamidine NAPAP, and the arylsulphonylarginine argatroban. The thrombin inhibitory peptides hirudin and hirulogs additionally span through the active and exosite domains of thrombin. The peptide hirugen and single-stranded DNA aptamers inhibit thrombin through exosite occupancy. These classes of antithrombotic agents still suffer from one or more of the following liabilities: (1) poor oral bioavailability due to the peptidic or oligonucleotidic nature of these agents, or high molecular weight or charged nature of the agents; (2) excessive bleeding complications; (3) poor selectivity towards thrombin versus other serine proteases (which may lead to severe and sometimes fatal hypotension and respiratory depression in animal models); (4) liver toxicity; or (5) cost effectiveness.

An alternative approach for inhibiting thrombin function is to inhibit factor Xa. Factor Xa associates with factor Va and calcium on a phospholipid membrane thereby forming a prothrombinase complex. This prothrombinase complex then converts prothrombin to thrombin (Claeson, Blood Coagulation and Fibrinolysis 5:411–436 (1994); Harker, Blood Coagulation and Fibrinolysis 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, Circulation 90(3):1522–1536 (1994); Harker, Blood Coagulation and Fibrinolysis 5 (Suppl 1):S47–S58 (1994)). Indeed, continuous generation of new thrombin rather than reexposure of preformed clot-bound thrombin is thought to be responsible in part for the phenomenon of reocclusion since markers of thrombin generation have been found to increase during and after thrombolytic treatment for myocardial infarction. Thus, it is now believed that increased thrombin activity associated with thrombolysis is due at least in part to new thrombin generation.

Specific protein factor Xa inhibitors, such as the leech-derived, 119-amino acid protein antistasin and the soft tick derived protein TAP (tick anticoagulant peptide) accelerated clot lysis and prevented reocclusion when given as adjuncts to thrombolysis (Mellott et al., Circulation Research 70:1152–1160 (1992); Sitko et al., Circulation 85:805–815 (1992)). U.S. Pat. No. 5,385,885, issued Jan. 31, 1995, discloses smooth muscle cell proliferation inhibitory activity of both TAP and antistasin. Additionally, TAP and antistasin have been shown to reduce experimental restenosis. These results suggest that factor Xa may play a role in the restenosis process through its effects upon thrombus formation or through its mitogenic potential (Ragosta et al., Circulation 89:1262–1271 (1994)). The peptide ecotin is another selective, reversible, tight-binding inhibitor of factor Xa that exhibits potent anticoagulant activity (Seymour et al., Biochemistry 33:3949–3959 (1994); PCT Published Application WO 94/20535, published Sep. 14, 1994). Ixodidae, argasin, and ancylostomatin are other representative peptidic factor Xa inhibitors isolated from animals that feed on blood (Markwardt, Thrombosis and Hemostasis 72:477–479 (1994)).

Non-peptide diamidino derivatives, such as (+)-(2S)-2-[4-[[(3S)-1-acetimidoyl-3-pyrrolidinyl]oxy]phenyl]-3-[7-amidino-2-naphthyl]propanoic acid hydrochloride pentahydrate (DX-9065a), exhibit anticoagulant activity (Tidwell et al., Thrombosis Research 19:339–349 (1980); Yamazaki et al., Thrombosis and Hemostasis 72:393–395 (1994); Hara et al., Thrombosis and Hemostasis 71:314–319 (1994); Nagahara et al., Journal of Medicinal Chemistry 37:1200–1207 (1994)). Synthetic amidino derivatives of phenylalanine and cycloheptanone have also shown potent factor Xa inhibition (Sturzebecher et al., Thrombosis Research 54:245–252 (1989)).

PCT Published Application WO 94/13693, published Jun. 23, 1994, discloses peptide analogs containing an aldehyde grouping. The application discloses that the analogs have substantial potency and specificity as inhibitors of mammalian factor Xa.

PCT Published Applications WO 93/15756, published Aug. 19, 1993, and WO 94/17817, published Aug. 18, 1994, disclose peptidyl arginine aldehydes that exhibit factor Xa and/or thrombin inhibitory activity.

PCT Published Applications WO 94/20526, published Sep. 15, 1994, discloses peptide derivatives having a C-terminal boronic acid group. The application discloses that these peptide derivatives possess protein-inhibiting activity and are potent thrombin inhibitors.

SUMMARY OF THE INVENTION

The present invention is directed to novel bis-arylsulfonylaminobenzamide derivatives having the Formula I (below). The compounds are formed by coupling arylsulfonylaminophenalkanoic acids with a diamine. Thus, also provided is a process for preparing compounds of Formula I.

The novel compounds of the present invention exhibit antithrombotic activity via factor Xa inhibition. Also provided is a method of treating thrombosis, ischemia, stroke, restenosis or inflammation in a mammal in need of such treatment comprising administering to said mammal an effective amount of a compound of Formula I. Further provided is a pharmaceutical composition comprising a compound of Formula I and one or more pharmaceutically acceptable carriers or diluents.

DETAILED DESCRIPTION OF THE PREFERRED EMBODIMENTS

The present invention provides novel compounds having the Formula I:

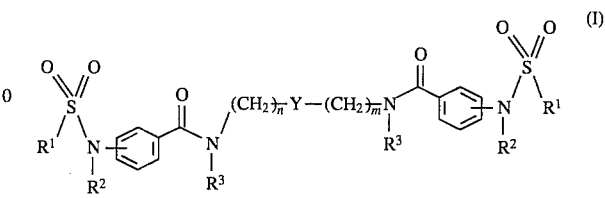

wherein each $R^1$ is independently one of alkyl, substituted alkyl, cycloalkyl, aryl, substituted aryl, heteroaryl or substituted heteroaryl;

each $R^2$ and $R^3$ is independently one of hydrogen, alkyl, aryl or arylalkyl;

Y is a bond, or is one of —$(CH_2)_p$—, cycloalkyl, aryl or $C_{2-10}$ heterocycle; and m, n and p are each independently 1 to 10.

Preferred compounds of the present invention are those of Formula I wherein each $R^1$ is independently one of $C_{6-12}$aryl or $C_{1-8}$alkyl; each $R^2$ and $R^3$ is independently one of hydrogen, $C_{1-8}$alkyl or $C_{6-12}$aryl; Y is a bond, or is one of —$(CH_2)_p$—, $C_{3-8}$ cycloalkyl, $C_{6-12}$ aryl or a 5 to 6 membered ring heterocycle; and m, n and p are each 1 to 5.

Most preferred are compounds of Formula I wherein each $R^1$ is the same and is either phenyl or naphthyl; each $R^2$ is the same and is one of hydrogen, $C_{1-5}$ alkyl, phenyl or naphthyl; each $R^3$ is the same and is one of hydrogen, $C_{1-5}$ alkyl, phenyl or naphthyl; Y is a bond, or is one of —$(CH_2)_p$—, $C_{3-8}$ cycloalkyl, $C_{6-10}$ aryl or 1,4-piperazinyl; and m, n and p are each independently 1 to 5.

Preferred heteroaryl groups in reference to $R^1$ include pyridinyl, thienyl, chromenyl, benzoxazolyl, quinazolinyl, quinolinyl and tetrahydroquinolinyl.

In general, any heterocyclic diamine may be employed to form compounds having a variety of heterocyclic groups at position Y. Examples of useful heterocyclic radicals are listed herein. Heteroaryl groups meeting the basic definition of "heterocycle" given herein may also be employed as the heterocycle Y.

The most preferred compounds include those compounds wherein each $R^1$ is 2-naphthyl, each $R^2$ and $R^3$ is each hydrogen, and Y is a bond, 1,4-substituted piperazinyl, or 1,3-substituted phenyl. Thus, compounds having the following structures are most preferred:

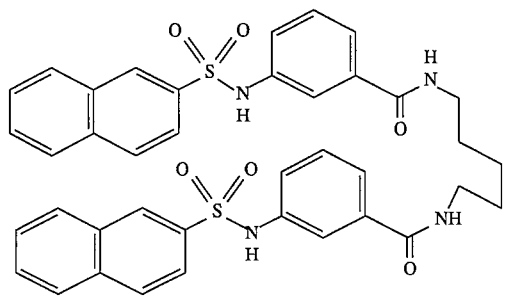

(9)

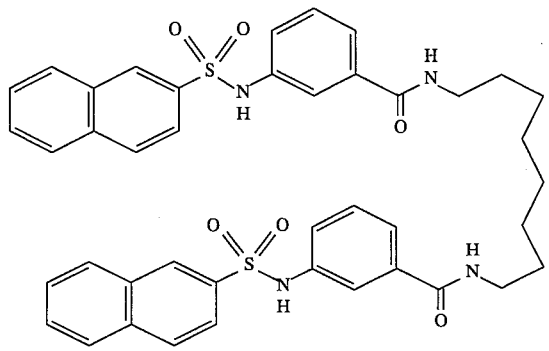

(10)

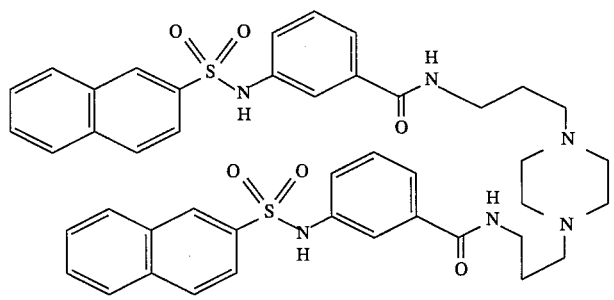

(11)

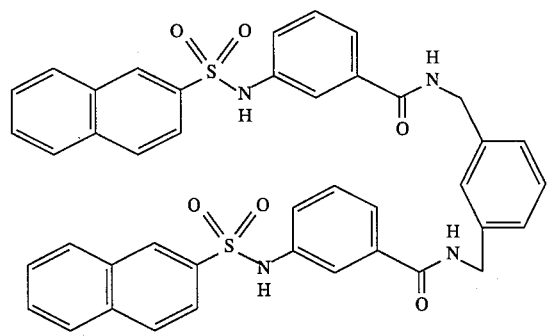

(12)

The term "alkyl" as employed herein includes both straight and branched chain radicals of up to 12 carbons, preferably 1–8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the various branched chain isomers thereof.

The term "substituted alkyl" as employed herein includes alkyl groups as defined above that have one, two or three halo substituents, or one $C_{6-10}$aryl, $C_{1-6}$alkyl($C_{6-10}$)aryl, halo($C_{6-10}$)aryl, $C_{3-8}$cycloalkyl, $C_{1-6}$alkyl($C_{3-8}$)cycloalkyl, $C_{2-8}$alkenyl, C2alkynyl, hydroxy and/or carboxy.

The term "cycloalkyl" as employed herein includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, $C_{1-6}$alkyl, alkoxy and/or hydroxy group.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "substituted aryl" as employed herein includes aryl groups, as defined above, that include one or two substituents on either the phenyl or naphthyl group such as $C_{1-6}$alkyl, $C_{3-8}$cycloalkyl, $C_{1-6}$alkyl($C_{3-8}$S)cycloalkyl, $C_{2-8}$alkenyl, $C_{2-8}$alkynyl, cyano, amino, $C_{1-6}$allcylamino, di($C_{1-6}$)alkylamino, benzylamino, dibenzylamino, nitro, carboxy, carbo($C_{1-6}$)alkoxy, trifluoromethyl, halogen, $C_{1-6}$alkoxy, $C_{6-10}$aryl($C_{1-6}$)alkoxy, hydroxy, $C_{6-10}$alkylthio, $C_{1-6}$alkylsulfinyl, $C_{1-6}$alkylsulfonyl, $C_{6-10}$arylthio, $C_{6-10}$arylsulfinyl and/or $C_{6-10}$arylsulfonyl.

The term "aralkyl" or "arylalkyl" as used herein by itself or as part of another group refers to $C_{1-6}$alkyl groups as discussed above having an aryl substituent, such as benzyl.

The terms "alkoxy," or "aralkoxy" includes any of the above alkyl or aralkyl groups linked to an oxygen atom.

The term "halogen" or "halo" as used herein by itself or as part of another group refers to chlorine, bromine, fluorine or iodine with chlorine being preferred.

The term "alkenyl" by itself or as part of another group as employed herein includes a carbon chain by itself or as part of another group of up to 16 carbons, preferably 2 to 10 carbons, containing one double bond such as propenyl, 2-butenyl, 3-butenyl, 2-pentenyl, 4-pentenyl and the like, and may include a halogen substituent such as I, Cl, or F.

The term "alkynyl" by itself or as part of another group as employed herein includes a carbon chain of up to 16 carbons, preferably 2 to 10 carbons, containing one triple bond such as 2-propynyl, 2-butynyl, 3-butynyl and the like.

The term "heterocycle" as employed herein refers to groups having 2 to 10 carbon atoms and having one or more 4, 5, 6, or 7 member saturated or unsaturated rings containing 1, 2, or 3 oxygen, nitrogen or sulfur heteroatoms (where examples of heterocyclic radicals are: tetrahydrofuran, 1,4-dioxane, 1,3,5-trioxane, pyrrolidine, piperidine, piperazine, imadazoline, isoindoline, chromane, isochromane, pyrazolidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam, and morpholine).

The term "heteroaryl" as employed herein refers to groups having 3 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl,β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The terms "substituted heteroaryl" or "optionally substituted heteroaryl," used in reference to $R^1$, refer to aryl groups, as defined above, having one or more substituents selected from halogen, $C_{1-6}$alkyl, $C_{1-6}$alkoxy,carboxy, amino, $C_{1-6}$alkylamino and/or di($C_{1-6}$)alkylamino.

The term "bond" as employed herein refers to a carbon to carbon single, double or triple bond.

The term "BOP" as employed herein refers to benzotriazol-1-yloxy-tris-(dimethylamino)phosphonium hexafluorophosphate.

The compounds of the present invention may be prepared by standard techniques as outlined in Scheme I.

Scheme I

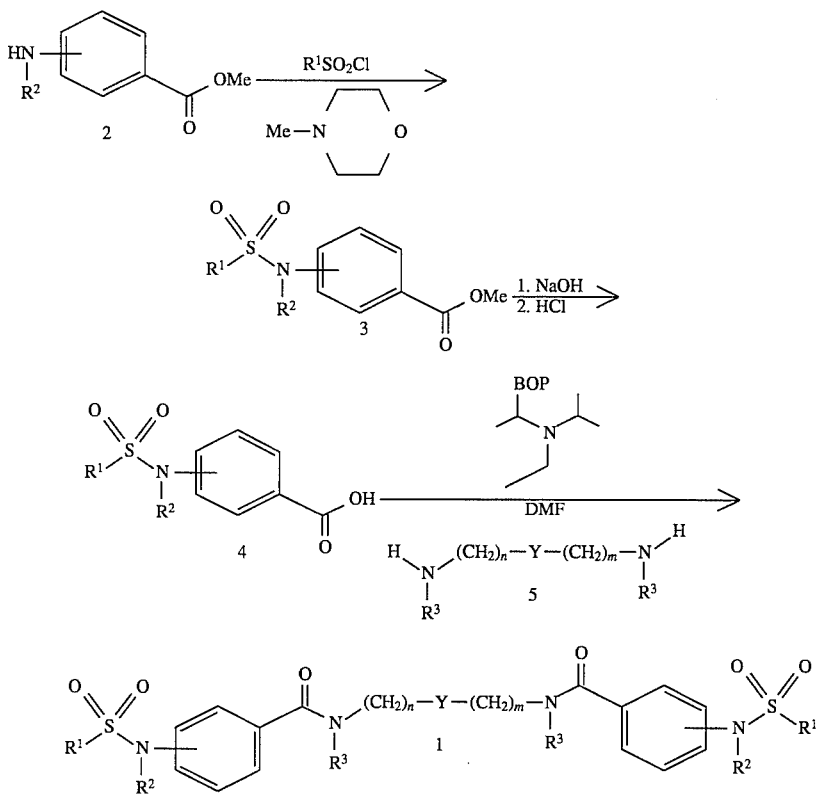

wherein $R^1$, $R^2$, $R^3$, Y, m and n are defined as above.

An aminobenzoic acid ester (that is optionally N-substituted) 2 is treated with an appropriate sulfonyl chloride under standard conditions to provide a N-sulfonylated derivative 3. Useful solvents for this step include methylene chloride, tetrahydrofuran, acetonitrile and dimethylformamide. The reaction proceeds at ambient temperature using a weak base, such as N-methylmorpholine, triethylamine or luditine. Hydrolysis of 3 with aqueous hydroxide, preferably at elevated temperature for a short time followed by acidification with aqueous acid such as 2N HCl gives the corresponding carboxylic acid 4. The final product is formed by coupling the carboxylic acid 4 with a diamine 5 using well-known peptide coupling procedures. Reagents for the coupling step include, most preferably, Castro's reagent (BOP)/diisopropylethylamine, or alternatively, hydroxybenzotriazole (HOBT), hydroxysuccinimide, 1,3-dicyclocarbodiimide (DCC), carbonyldiimidazole (CDI), isobutylchloroformate/$NEt_3$, or diphenylphosphorylazide (DPPA)/$NEt_3$. The coupled dimeric product is the major product after usual workup.

Unsymmetrical products can be formed by employing a mixture of two distinct carboxylic acids (4), and thereafter separating unsymmetrical product from dimeric product. More preferably, one of the amino groups of the diamine reactant is first protected with an amino protecting group, such as phenylmethoxycarbonyl (Cbz) or t-butyloxycarbonyl (BOC). See Greene, T. W., Protecting Groups in Organic Synthesis, John Wiley, New York (1981). Thereafter, a first carboxylic acid can be condensed with the mono-protected diamine. The amino-protecting group is subsequently removed and the resulting intermediate is reacted with a second carboxylic acid to form a diarylsulfonylaminobenzamide derivative.

The compounds of the present invention are distinguished by their ability to preferentially inhibit factor Xa in comparison to thrombin and/or plasmin. As factor Xa inhibitors, the compounds of the present invention inhibit thrombin production. Therefore, the compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections, and cancer; myocardial infarction; stroke; coronary artery bypass; hip replacement; and thrombus formation resulting from either thrombolytic therapy or percutaneous transluminal coronary angioplasty (PCTA). The compounds of the present invention may also be used as an anticoagulant in extracorporeal blood circuits. By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses, such as edema; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

The compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The compounds of the present invention may be administered in an effective amount within the dosage range of about 0.1 to about 500 mg/kg, preferably between 0.1 to 10 mg/kg body weight, on a regimen in single or 2–4 divided daily doses.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, drageemaking, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts and alkaline solutions. Especially preferred alkaline salts are ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Preparation of Methyl 3-Aminobenzoate (6)

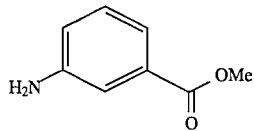

A mixture of methyl 3-nitrobenzoate (18.1 g, 0.10 mmol) in ethanol/tetrahydrofuran (9:1) and 1.8 g of 10% Pd/C was hydrogenated under a hydrogen atmosphere at atmospheric pressure and ambient temperature for 24 hr. The reaction mixture was filtered through Celite (Celite is a registered trademark of the Johns-Manville Product Corporation for diatomaceous earth) and washed with ethanol. The solvent was removed in vacuo to give the title compound as a pale yellow solid (14.7 g; 97% yield) which was used as is in the next reaction. $^1$H-NMR (200 MHz; CDCl$_3$) δ7.43 (d, 1H, J=7.6 Hz), 7.35 (t, 1H, J=2.3 Hz), 7.25 (d, 1H, J=2.3 Hz), 7.19 (d, 1H, J=7.7 Hz), 3.89 (s, 3H), 3.7 ppm (bs, 2H).

EXAMPLE 2

Methyl 3-((2-Naphthalenyl)sulfonylamino)benzoate (7)

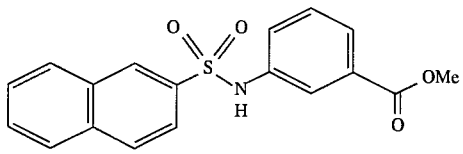

To 5.0 g (33 mmol) of methyl 3-aminobenzoate (6) in 70 mL of methylene chloride containing 4.0 mL (36 mmol) of N-methylmorpholine was added 7.49 g (33 mmol) of 2-naphthalenesulfonyl chloride. After stirring at room temperature overnight, the reaction mixture was quenched with 1N HCl (100 mL). The suspension was dissolved in ca. 250 mL of tetrahydrofuran and enough ether was added to induce phase separation. The organic extract was washed with saturated sodium chloride solution (2 x). The organic phase was dried (MgSO$_4$), and concentrated to give 11.0 g (97% yield) of the title compound as a pale yellow solid: $^1$H-NMR (200 MHz; DMSO-d$_6$) δ8.46 (s, 1H), 8.13 (t, 2H), 7.99 (d, 1H), 7.55–7.75 (m, 5H), 7.43 (dd, 21H), 7.38 (d, 1H), 3.79 ppm (s, 3H).

EXAMPLE 3

Preparation of 3-((2-Naphthalenyl)sulfonylamino)benzoic acid (8)

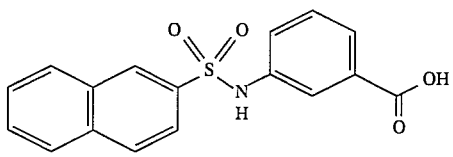

A solution of 10.8 g (31.7 mmol) of methyl 3-((2-naphthalenyl)sulfonylamino)benzoate (7) in 100 mL of 1N NaOH was stirred at 50° C. for 20 min. The reaction mixture was quenched with excess 2N HCl, diluted with tetrahydrofuran to dissolve the suspension. Ether was added to induce phase separation. The organic extract was dried (MgSO$_4$) and the solvent removed in vacuo. Trituration from ether/tetrahydrofuran/hexane gave 10.0 g of the title compound: $^1$H-NMR (200 MHz, DMSO-d$_6$)δ8.45 (s, 1H), 8.13 (t, 2H), 7.99 (d, 1H), 7.54–781 (m, 5H), 7.77–7.43 ppm (m, 2H); Mass spectrum (MALDI-TOF) Calcd. for C$_{17}$H$_{13}$NO$_4$S: 328.1 (M+H) and 350.0 (M+Na). Found: 328.7 (M+H), 349.8 (M+Na).

EXAMPLE 4

Preparation of 1,5-di[3-(2-naphthalenylsulfonylamino)benzamido]pentane

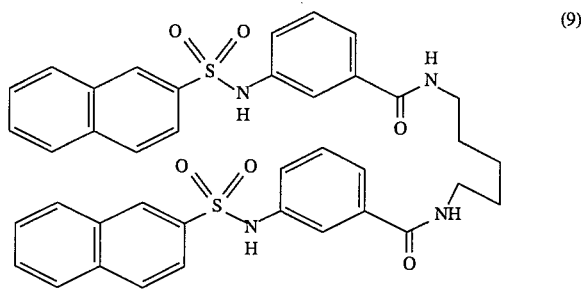

(9)

To a solution of 160 mg (0.469 mmol) of 3-((2-naphthalenyl)sulfonylamino)benzoic acid (8) in 3 mL of N,N-dimethylformamide was added 1 mL (0.5 mmol) of 0.5 M BOP (Castro's Reagent). Then 500 mL of diisopropylethylamine was added. After 5 min, the solution was transferred dropwise to a solution of 1,5-diaminopentane (55 μL; 0.469 mmol). After 30 min, the reaction mixture was quenched with saturated sodium bicarbonate solution and extracted into ethyl acetate (3×3 mL). The organic phase was washed with saturated sodium bicarbonate solution (4×5 mL). The organic phase was concentrated and purified by silica gel chromatography using ethyl acetate/methylene chloride (1:1) to give the title compound: $^1$H-NMR (300 MHz; DMSO-d$_6$) δ10.5 (bs, 2H), 8.43 (d, 2H, J=1.2 Hz), 8.36 (t, 2H, J=5.4 Hz), 8.10 (t, 4H, J=8.7 Hz), 7.97 (t, 2H, t J=7.7 Hz)), 7.77 (dd, 2H, J=1.8, 8.7 Hz), 7.59–7.71 (m, 6H), 7.39–7.43 (m, 2H), 7.25 (d, 2H, J=5.1 Hz), 3.16 (q, 4H, J=6.7 Hz), 1.45 (pentet, 4H, J=7.1 Hz), 1.25 ppm (2H, pentet, J=7.2 Hz).

EXAMPLE 5

Preparation of 1,8-di[3-(2-naphthalenylsulfonylamino)benzamido]octane

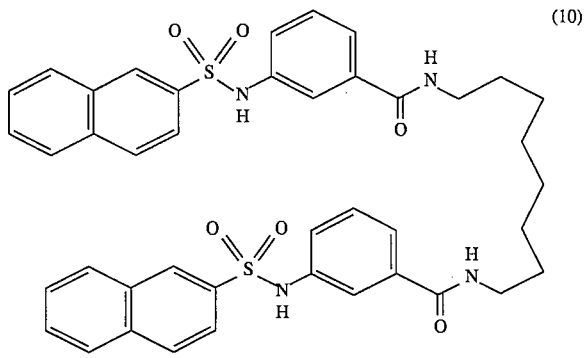
(10)

In a manner identical to the procedure of Example 4 the title compound was prepared substituting 1,8-diaminooctane for 1,5-diaminopentane. Purification was achieved by crystallization from methylene chloride/ether/hexane/ethyl acetate: $^1$H-NMR (300 MHz, DMSO-$d_6$) $\delta$10.5 (bs, 2H), 8.44 (d, 2H, 1 Hz), 8.36 (t, 2H, J=5.3 Hz), 8.09 (t, 4H, J=8.6 Hz), 7.99 (d, 2H, J=7.8 Hz), 7.77 (dd, 2H, J=1.8, 8.6 Hz), 7.59–7.70 (m, 6H), 7.39–7.44 (m, 2H), 7.23–7.29 (m, 4H), 3.16 (q, 4H, J=6.6 Hz), 1.44 (br pentet, 4H), 1.24 ppm (br s, 8H).

EXAMPLE 6

Preparation of 1,4-di-[3-(2-naphthalenylsulfonylamino)benzamidopropyl]piperazine

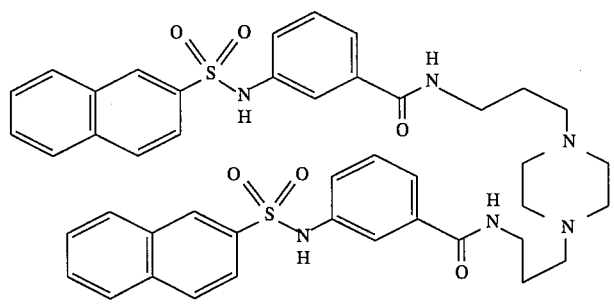

In a manner identical to the procedure of Example 4, the title compound was prepared substituting 1,4-bis(3-aminopropyl)piperazine for 1,5-diaminopentane. Purification was achieved by trituration from ethyl acetate/methylene chloride/ether/hexane to give the title compound: $^1$H-NMR (300 Mz; DMSO-$d_6$) $\delta$8.4 (d, 2H, J=1 Hz), 8.37 (t, 2H, J=5.4 Hz), 8.02–8.10 (m, 4H), 7.97 (d, 2H, J=7.4 Hz), 7.75 (dd, 2H, J=1.8, 8.6 hz), 7.58–7.68 (m, 4H), 7.53 (s, 2H), 7.31–7.33 (m, 2H), 7.16–7.23 (m, 4H), 3.19 (q, 4H, 5.7 Hz), 2.23–2.28 (m, 10H), 1.59 ppm (pentet, 4H), J=6.6 Hz).

EXAMPLE 7

Preparation of 1,3-di-[3-(2-naphthalenylsulfonylamino)benzamidomethyl]benzene

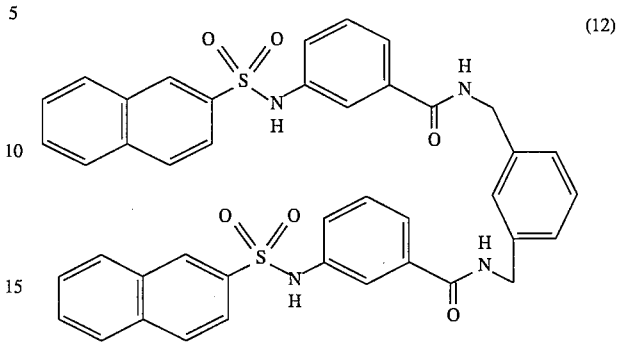
(12)

To a solution of 230 mg (0.7 mmol) of 3-((2-naphthalenyl)sulfonylamino)benzoic acid, (4) Castro's reagent (310 mg, 0.7 mmol), and triethylamine (0.3 mL) in anhydrous dimethylformamide (5 mL) was added meta-xylylenediamine (680 mg, 5 mmol). After stirring at ambient temperature for 3 h, the reaction mixture was diluted with 200 mL of ethyl acetate and then washed successively with saturated NaHCO$_3$ (2×50 mL), brine (3×50 mL), and 0.5N HCl (4×50 mL). The organic phase was dried over Na$_2$SO$_4$ and concentrated to give 100 mg (38% yield) of the title compound as a white solid: $^1$H-NMR $\delta$10.5 (bs, 2H), 8.96 (t, 2H, J=6 Hz), 8.44 (d, 2H, J=1 Hz), 8.09 (t, 4H, J=8 Hz), 7.98 (d, 2H, J=8 Hz), 7.77 (dd, 2H, J=2, 9 Hz), 7.60–7.70 (m, 6H), 7.45–7.50 (m, 2H), 7.10–7.28 (m, 6H), 4.37 (d, 4H). Mass spectrum Calcd. for C$_{42}$H$_{24}$H$_4$O$_6$S$_2$: 777.9 (M+Na). Found: 778.0.

EXAMPLE 8

In Vitro Inhibition of Purified Enzymes (11)

The ability of the compounds of the present invention to act as inhibitors of thrombin, factor Xa and plasmin catalytic activity was assessed by determining the concentration which inhibited enzyme activity by 50% using purified human enzymes. The concentration of added inhibitor that caused a 50% decrease in the initial rate of hydrolysis was defined as the IC$_{50}$ value.

All assays are based on the ability of the test compound to inhibit the hydrolysis of a peptide p-nitroanilide substrate. In a typical experiment, appropriate substrate is prepared in DMSO, and diluted into an assay buffer consisting of 50mM HEPES and 130 mM NaCl at a pH of 7.5. The final concentration for each of the substrates is listed below. All substrate concentrations are at least 10 fold lower than $K_m$ to insure inhibition is competitive. Test compounds are prepared as 1 mg/ml solutions in DMSO, and three additional 10-fold dilutions in DMSO are prepared. Enzyme solutions are prepared at the concentrations listed below in assay buffer.

In a typical $IC_{50}$ determination, into each well of a 96 well plate is pipetted 280 uL of substrate solution, 10 μL of inhibitor solution, and the plate is allowed to thermally equilibrate at 37° C. in a Molecular Devices Plate Reader for at least 10 minutes. Reactions are initiated by the addition of a 20 μL aliquot of enzyme, and the absorbance increase at 405 nm is recorded for 15 minutes. Data corresponding to less than 10% of the total substrate hydrolysis is used in the calculations. The ratio of the velocity (rate of the change in absorbance as a function of time) for a sample containing no inhibitor is divided by the velocity of a sample containing inhibitor, and is plotted as a function of inhibitor concentration. The inverse of the slope is the concentration of inhibitor which produces a 50% decrease in activity of the enzyme. This concentration is referred to as the $IC_{50}$.

Thrombin

Thrombin activity was assessed as the ability to hydrolyse the substrate N-benzoyl-Phe-Val-Arg-p-nitroanilide (Bz-Phe-Val-Arg-pNa), and was obtained from Sigma Chemical Company (St. Louis, Mo.). Substrate solutions were prepared at a concentration of 60 μM (60 μM<<$K_m$=1.2 mM) in assay buffer. Final DMSO concentration was 0.3%. Purified human α-thrombin was obtained from Enzyme Research Laboratories, Inc., and was diluted into assay buffer to a concentration of 1.2 μM. Final reagent concentrations were: [thrombin]=36 nM, [Bz-Phe-Val-Arg-pNa]=66 μM, [inhibitor]=60 to 0.06 μM.

Factor Xa

Factor Xa activity was assessed as the ability to hydrolyse the substrate Bz-Ile-Glu-Gly-Arg-pNa, and was obtained from Sigma. Substrate solutions were prepared at a concentration of 26 μM (26 μM<<$K_m$=1.3 mM) in assay buffer. Final DMSO concentration was 0.3%. Activated factor Xa was obtained from Enzyme Research Laboratories, Inc., and was diluted into assay buffer to a concentration of 1.2 μM. Final reagent concentrations were: [Factor Xa]=10 nM, [Bz-Ile-Glu-Gly-Arg-pNa]=26 μM, [inhibitor]=60 to 0.06 μM.

Plasmin Plasmin activity was assessed as the ability to hydrolyse the substrate Tos-GlyoPro-Lys-pNa, and was obtained from Sigma. Substram solutions were prepared at a concentration of 22 μM (22 μM<<$K_m$=240 μM) in assay buffer. Final DMSO concentration was 0.3%. Purified human plasmin was obtained from Enzyme Research Laboratories Inc, and was diluted into assay buffer to a concentration of 1.2 μM. Final reagent concentrations were: [plasmin]=15 nM, [Bz-Ile-Glu-Gly-Arg-pNa]=26 μM, [inhibitor] =60 to 0.06 μM.

The results obtained employing the compounds of Examples 4 through 7 are given in Table 1.

TABLE 1

| Compound of Example | Factor Xa Inhibition $IC_{50}$ (μM) | Thrombin % Inhibition at 6 μM | Plasmin % Inhibition at 6 μM |
|---|---|---|---|
| 4 | 3 μM | 0% | 0% |
| 5 | 2.1 μM | 20% | 0% |
| 6 | 5.2 μM | 0% | 0% |
| 7 | 2.4 μM | 20% | 40% |

The results indicate that the compounds of the present invention, and specifically the compounds of Examples 4 through 7 are highly selective and potent inhibitors of factor Xa.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having Formula I:

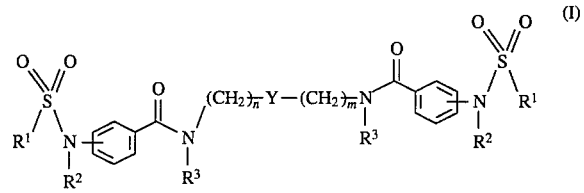

wherein
each $R^1$ is independently one of alkyl, substituted alkyl cycloalkyl, aryl, or substituted aryl;
each $R^2$ and $R^3$ is independently one of hydrogen, alkyl, aryl or arylalkyl;
Y is a bond, or is one of —$(CH_2)_p$—, cycloalkyl, or aryl; and
m, n and p are each independently 1 to 10.

2. The compound of claim 1, wherein
each $R^1$ is independently one of $C_{6-12}$aryl or $C_{1-8}$alkyl;
each $R^2$ and $R^3$ is independently one of hydrogen, $C_{1-8}$alkyl or $C_{6-12}$aryl;
Y is a bond, or is one of —$(CH_2)_p$—, $C_{3-8}$cycloalkyl, or $C_{6-12}$ aryl; and
m, n and p are each independently 1 to 5.

3. The compound of claim 2, wherein
each $R^1$ is the same and is one of phenyl, naphthyl or tetrahydronaphthyl;
each $R^2$ is the same and is one of hydrogen, $C_{1-5}$alkyl, phenyl or naphthyl;
each $R^3$ is the same and is one of hydrogen, $C_{1-5}$alkyl, phenyl or naphthyl;
Y is a bond, or is one of —$(CH_2)_n$—, $C_{3-8}$cycloalkyl, or $C_{6-10}$aryl; and
m, n and p are each independently 1 to 5.

4. The compound of claim 3 having the structure:

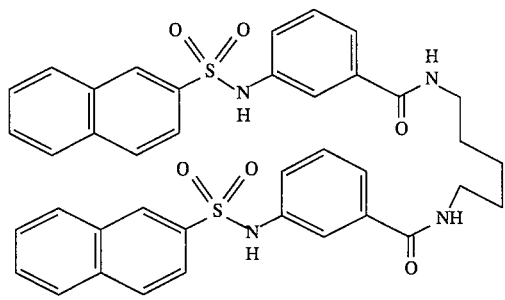
(9)

5. The compound of claim 3 having the structure:

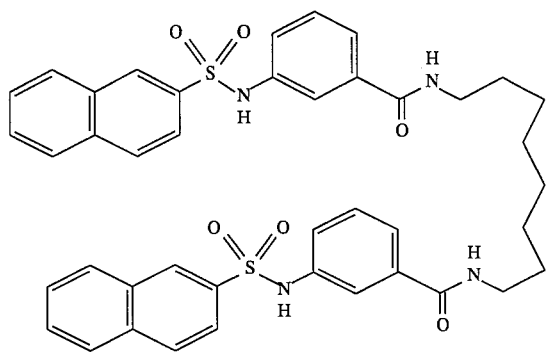
(10)

6. The compound of claim 3 having the structure:

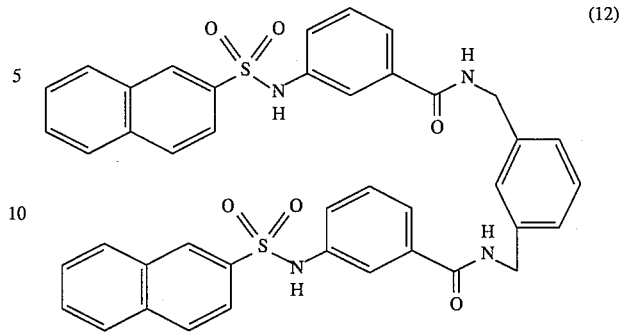
(12)

7. A pharmaceutical composition comprising a compound of claim 1.

8. The pharmaceutical composition of claim 7 further comprising a pharmaceutically acceptable carrier or diluent.

9. A method of treating thrombosis, ischemia, stroke, restenosis or inflammation comprising administering to a mammal in need of said treatment a therapeutically or prophylactically effective amount of the compound of claim 1.

10. A method of treating thrombosis, ischemia, stroke, restenosis or inflammation comprising administering to a mammal in need of said treatment a therapeutically or prophylactically effective amount of one of the compounds of claims 4, 5 or 6.

* * * * *